US006350745B1

(12) United States Patent
Coburn et al.

(10) Patent No.: US 6,350,745 B1
(45) Date of Patent: Feb. 26, 2002

(54) THROMBIN INHIBITORS

(75) Inventors: Craig A. Coburn, Royersford; Christopher S. Burgey, Plymouth Meeting, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/585,740

(22) Filed: Jun. 2, 2000

Related U.S. Application Data

(60) Provisional application No. 60/137,644, filed on Jun. 4, 1999.

(51) Int. Cl.[7] ................. C07D 498/04; A61K 31/5365; A61P 7/02
(52) U.S. Cl. ...................................... 514/230.5; 544/91
(58) Field of Search .......................... 544/91; 514/230.5

(56) References Cited

U.S. PATENT DOCUMENTS

| | | | |
|---|---|---|---|
| 4,296,114 A | 10/1981 | Appleton et al. ...... | 424/248.52 |
| 5,260,307 A | 11/1993 | Ackermann et al. ........ | 514/323 |
| 5,272,158 A | 12/1993 | Hartman et al. ............ | 514/323 |
| 5,405,854 A | 4/1995 | Ackermann et al. ........ | 514/315 |
| 5,459,142 A | 10/1995 | Tone et al. .................. | 514/252 |
| 5,510,369 A | 4/1996 | Lumma et al. ............. | 514/422 |
| 5,585,385 A | 12/1996 | Natsugari et al. ........... | 514/300 |
| 5,602,253 A | 2/1997 | Antonsson et al. ......... | 544/330 |

FOREIGN PATENT DOCUMENTS

| | | |
|---|---|---|
| EP | 0 262 096 A1 | 3/1988 |
| EP | 0 509 769 A2 | 10/1992 |
| EP | 0 648 780 A1 | 4/1995 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 98/17274 | 4/1998 |
| WO | WO 99/15169 | 4/1999 |

OTHER PUBLICATIONS

Bernstein, Peter R., et al., "Nonpeptidic Inhibitors of Human Leukocyte Elastase . . . ," *J. Med. Chem.*, vol. 37, pp. 3313–3326, 1994.
Temple, Carroll Jr. et al, "Antimitotic Agents: Ring Analogues and Derivatives of Ethyl . . . ," *J. Med. Chem.*, vol. 35, pp. 4809–4812, 1992.
Mack, Helmut, et al., "Design, Synthesis and Biological Activity of Novel Rigid Amidino–Phenylalanine Derivatives as Inhibitors of Thrombin," *J. Enzyme Inhibition*, vol. 9, pp. 73–86, 1995.
Semple, Edward, et al., "Design Synthesis, and Evolution of a Novel, Selective, and Orally Bioavailable Class of Thrombin Inhibitors: . . . ," *J. Med. Chem.*, vol. 39, pp. 4531–4536, 1996.
Edwards, Philip D., et al., "Design, Synthesis, and Kinetic Evaluation of a Unique Class of Elastase Inhibitors, the Peptidyl . . . ," *J. Am. Chem. Soc.*, vol. 114, pp. 1854–1863, 1992.

Brown, Frederick, J., et al., "Design of Orally Active, Non–Peptidic Inhibitors of Human Leukocyte Elastase," *J. Med. Chem.*, vol. 37, pp. 1259–1261, 1994.
Shimada et al., Chem. Pharm. Bull., vol. 31(12) (1983), pp. 4247–4258, "Intramolecular diels—alder reaction of alkenyl oxazole–5–carbamates and N–alkenyl–oxazole–5–carboxamides".
Edmunds et al., Annual Reports in Medicinal Chemistry, vol. 31 (1996), pp. 51–60, "Section II. Cardiovascular and Pulmonary Diseases: Chap. 6. Thrombin and Factor Xa Inhibition".

*Primary Examiner*—Mukund J. Shah
*Assistant Examiner*—Kahsay Habte
(74) *Attorney, Agent, or Firm*—Richard S. Parr; Melvin Winokur

(57) ABSTRACT

Compounds of the invention, useful as thrombin inhibitors and having therapeutic value in for example, preventing coronary artery disease, have the following structure:

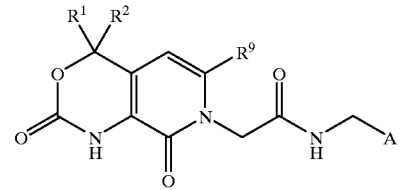

or a pharmaceutically acceptable salt thereof, wherein A is

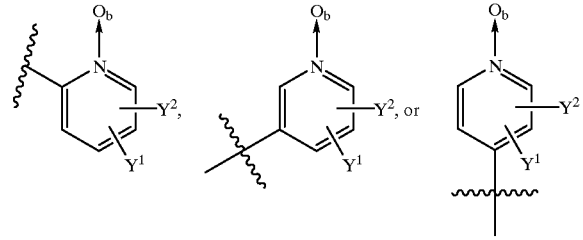

wherein
$Y^1$ and $Y^2$ are independently
hydrogen,
$C_{1-4}$ alkyl,
$C_{1-4}$ alkoxy,
$F_uH_vC(CH_2)_{0-1}$ O—, wherein u and v are either 1 or 2, provided that when u is 1, v is 2, and when u is 2, v is 1,
$C_{3-7}$ cycloalkyl,
thio $C_{1-4}$ alkyl,
$C_{1-4}$ sulfinylalkyl,
$C_{1-4}$ sulfonylalkyl,
halogen
cyano, or
trifluoromethyl, and
wherein b is 0 or 1.

8 Claims, No Drawings

THROMBIN INHIBITORS

CROSS REFERENCE TO RELATED APPLICATIONS

The present application claims priority of U.S. provisional application Ser. No. 60/137,644, filed Jun. 4, 1999.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.,* (1992) vol. 114, pp. 1854–63, describes peptidyl α-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.,* Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition,* Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure:

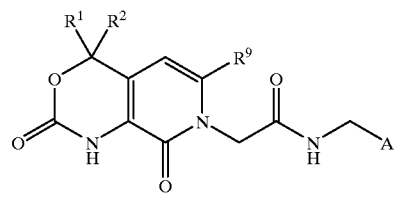

or a pharmaceutically acceptable salt thereof, wherein

A is

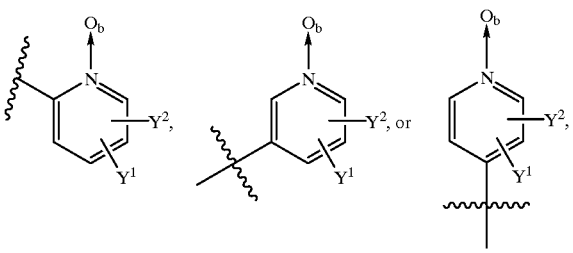

wherein
  $Y^1$ and $Y^2$ are independently
    hydrogen,
    $C_{1-4}$ alkyl,
    $C_{1-4}$ alkoxy,
    $F_u H_v C(CH_2)_{0-1} O$—, wherein u and v are either 1 or 2, provided that when u is 1, v is 2, and when u is 2, v is 1,
    $C_{3-7}$ cycloalkyl,
    thio $C_{1-4}$ alkyl,
    $C_{1-4}$ sulfinylalkyl,
    $C_{1-4}$ sulfonylalkyl,
    halogen
    cyano, or
    trifluoromethyl, and
  wherein b is 0 or 1; and
$R^1$ and $R^2$ are independently
  hydrogen,
  phenyl, unsubstituted or substituted with one or more of $C_{1-4}$ alkyl, $C_{1-4}$ alkoxy, halogen, hydroxy, COOH, $CONH_2$, $CH_2OH$, $CO_2R^8$, where $R^8$ is $C_{1-4}$ alkyl, or $SO_2NH_2$,
  $CHR^6R^7$
    wherein $R^6$ and $R^7$ are independently
      hydrogen, unsubstituted $C_{1-4}$ alkyl,
      $C_{1-4}$ alkyl substituted with OH, COOH, $NH_2$, aryl, $CF_3$,
      $C_{3-7}$ cycloalkyl,
  $CF_3$
  $CH_2C_{3-7}$ cycloalkyl, unsubstituted or substituted with aryl,
  $C_{7-12}$ bicyclic alkyl, or
  $C_{10-16}$ tricyclic alkyl; and
$R^9$ is $C_{1-4}$ alkyl.

In a class of compounds, A is

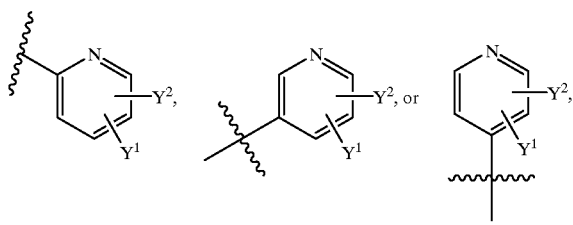

A subclass of the class of compounds of the invention, or a pharmaceutically acceptable salt thereof, includes those wherein A is

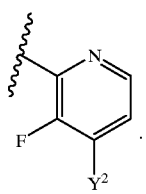

A group of this subclass of compounds, or a pharmaceutically acceptable salt thereof, includes those wherein
$R^1$ and $R^2$ are independently
—$CH_3$,
—$CH_2CH(CH_3)_2$,
—$CH_2CH_2$,
—$CH(CH_3)_2$, or

$R^9$ is $CH_3$.

An example of this group is listed below. The compound has a Ki of less than 100 nM. The value is determined according to the in vitro assay described later in the specification.

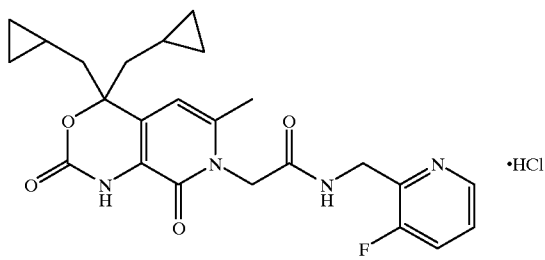

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic rings may also be referred to hereinafter as "heteroaryl" rings.

The pharmaceutically-acceptable salts of the compounds of Formula I (in the lorm ol water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases.

Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

ABBREVIATIONS

| Designation | |
|---|---|
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| HBT(HOBT or HOBt) | t-hydroxybenzotriazole hydrate |
| HOAT | 1-hydroxy-7-azabenzotriazole |
| | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloric |
| EDC | 1-ethyl-3-(3-dimethylaminopropyl) carbodiimide hydrochloride |
| | Amino Acid |
| Ile | Isoleucine |
| Phe | Phenylalanine |
| Pro | Proline |
| Ala | Alanine |
| Val | Valine |
| | Other |
| (BOC)$_2$O(BOC$_2$O) | di-t-butyl dicarbonate |
| n-BU$_4$N+F- | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DCM | dichloromethane |
| CDI | carbonyl diimidazole |
| DIPEA | diisopropylethylamine |
| MCPBA | Meta-chloroperbenzoic acid |

-continued

| Designation | |
|---|---|
| TMSCN | trimethylsilyl cyanide |
| LDA | lithium diisopropylamide |
| TBSCl | tert-butyldimethylsilyl chloride |
| TBAF | tetrabutylammonium fluoride |
| DBU | 1,8-diazabicyclo[5.4.0]undec-7-ene |
| TMEDA | N,N,N',N'-tetramethylenediamine |

In vitro Assay for Determining Proteinase Inhibition

Assays of human α-thrombin and human trypsin were performed by the methods substantially as described in *Thrombosis Research,* Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human ☐thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$ M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1:

$$V_o/V_i=1+[I]/K_i \qquad (1).$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki).

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Prodrugs of described compounds are compound derivatives which, when absorbed into the bloodstream of a warm-blooded animal, cleave in such a manner as to release the drug form and permit the drug to afford improved therapeutic efficacy. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the thrombin inhibitors may be coupled to a class of biodegradable polymers useful in achieving control led release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

General Procedure for Making Compounds of the Invention

Compounds may be prepared, for example, by a common condensation reaction between a group having a carboxylic acid moiety and a group having an amino moiety, forming a peptide or amide bond. Compounds may be prepared by other means however, and suggested starting materials and procedures described below are exemplary only and should not be construed as limiting the scope of the invention.

In general, compounds having the general structure

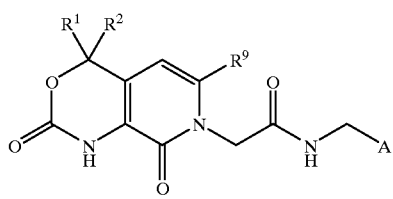

wherein the variables have the above-described meanings, can be prepared by reacting

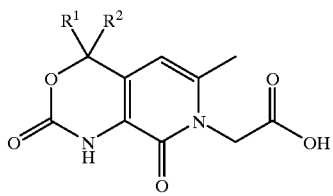

with

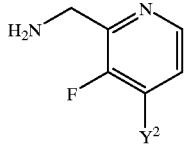

under conditions suitable for forming an amide bond between the acid and the amine.

Suitable carboxylic acid starting materials for

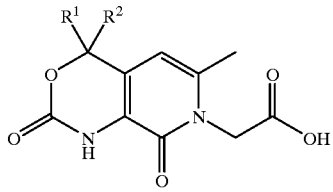

may be prepared according to the following procedures.

General Synthesis

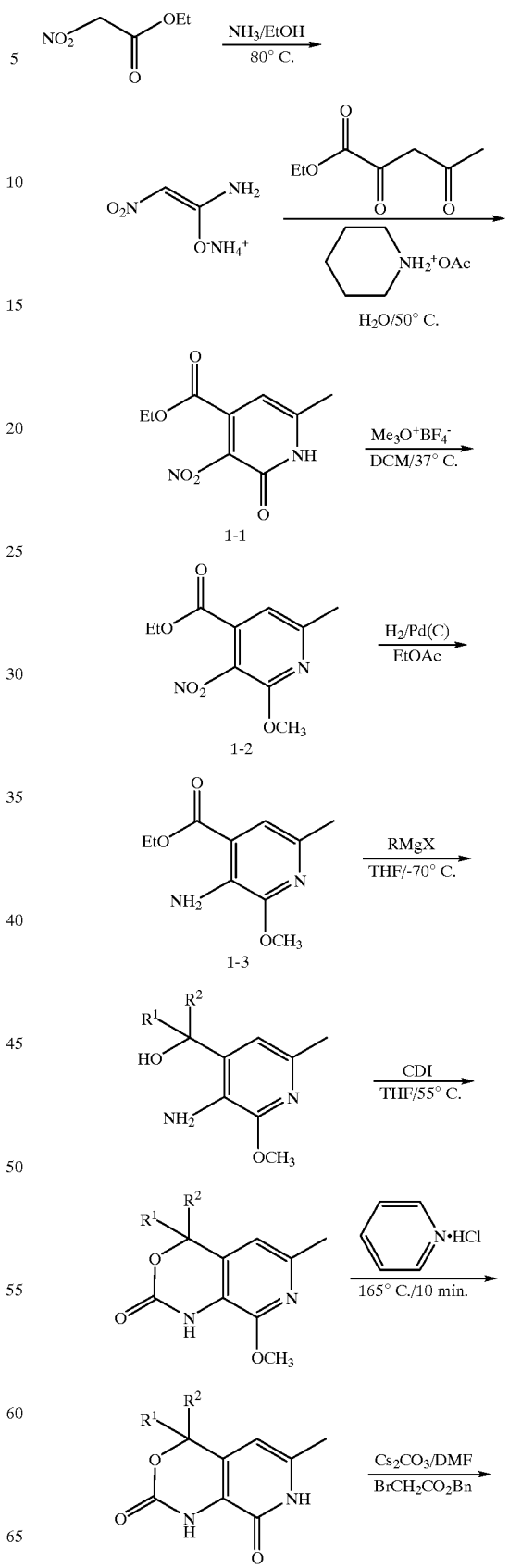

-continued

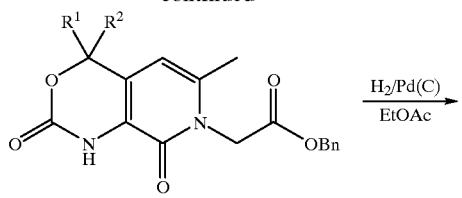

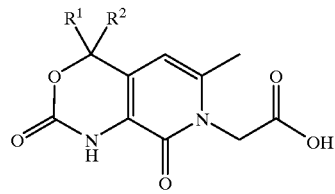

Compounds of the invention are then formed by reacting the carboxylic acid with

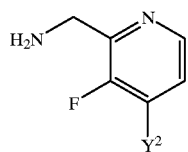

as shown below:

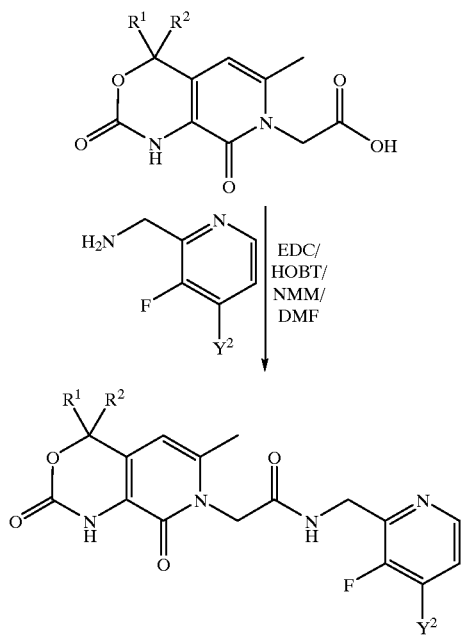

wherein

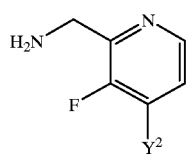

can be, for example, of 2-aminomethyl-3-fluoropyridine and related fluoropyridine derivatives, in order to form the finished product. 2-aminomethyl-3-fluoropyridine is prepared as follows:

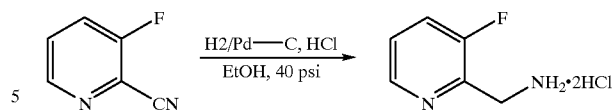

Synthesis of 2-aminomethyl-3-fluoropyridine begins with catalytic reduction of 2-cyano-3-fluoropyridine (Sakamoto et al., Chem. Pharm. Bull. 33(2) 565–571 (1985)) using palladium on carbon which provides 2-aminomethyl-3-fluoropyridine B as the dihydrochloride salt.

The coupling of 2-aminomethyl-3-fluoropyridine B and 3-(2,2-difluoro-2-(2-pyridyl)ethylamino)-6-methylpyrazin-2-one-1-acetic acid is carried out in DMF using EDC, HOBT and triethylamine. Addition of water precipitates the product which is then purified by silica gel chromatography to give the title compound as a slightly colored solid. Conversion to its hydrochloride salt can be carried out by treating an ethyl acetate solution with two equivalents of 1M HCl in ethyl acetate, followed by filtration.

2-Aminomethyl-3-fluoropyridine (B) as a dihydrochloride salt

A stirred solution of 6.11 g (50.1 mmol) of 2-cyano-3-fluoropyridine in 250 mL of ethanol and 12.5 mL (150 mmol) of conc. HCl was hydrogenated over 1.90 g of 10% palladium on carbon at 40 psi for 16 h. The catalyst was removed by filtration and the solvents removed at reduced pressure. The resulting solid was diluted with acetonitrile and filtered to give 8.0 g of the title compound as an off-white solid: $^1$H NMR (CD$_3$OD) δ8.48 (d, 1H, 4.8 Hz), 7.69 (td,1H, 9.2, 1.1 Hz), 7.68 (ddd, 1H, 8.8, 4.4, 4.4 Hz), 4.34 (s, 2 H).

Typically, solution phase amide couplings may be used to form the final product, but solid-phase synthesis by classical Merrifield techniques may be employed instead. The addition and removal of one or more protecting groups is also typical practice.

Compounds having different groups at variable A can be prepared by coupling alternative amino derivatives

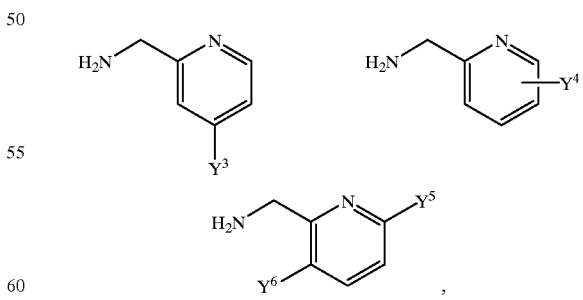

where $Y^3$ is Cl or Br, $Y^4$ is hydrogen or $C_{1-4}$ alkyl, $Y^5$ is CH$_3$, and $Y_6$ is phenyl, —OCH$_2$COOEt, or —OCH$_2$C(CH$_3$)$_2$OH, using the coupling procedure described for coupling

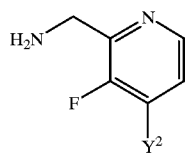
to the carboxylic acid. Alternative amino derivatives and methods for preparing amino derivatives are described below.
1)
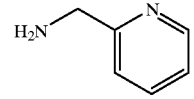
is commercially available.
2)
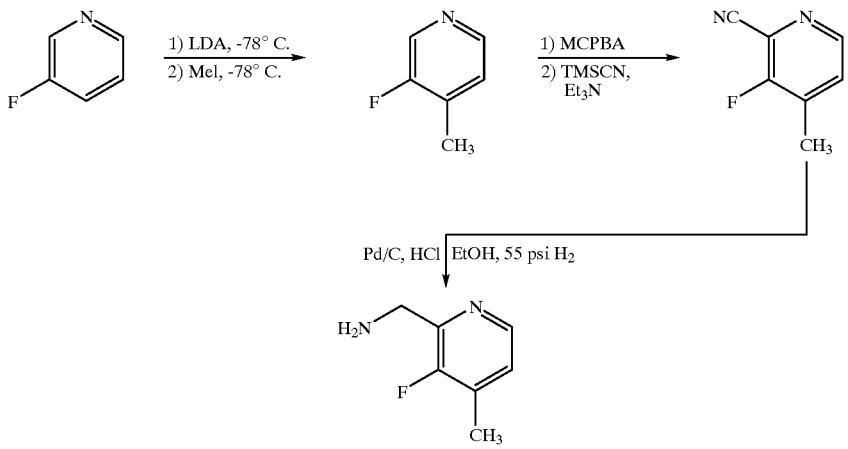
3)
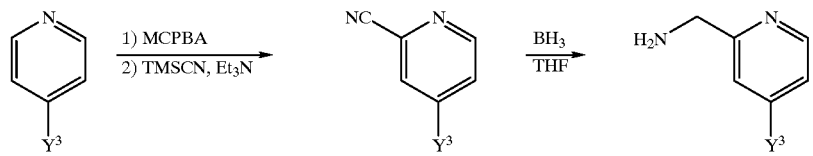
4)
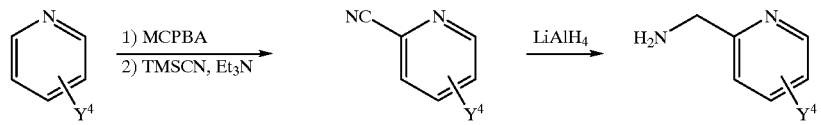
5)
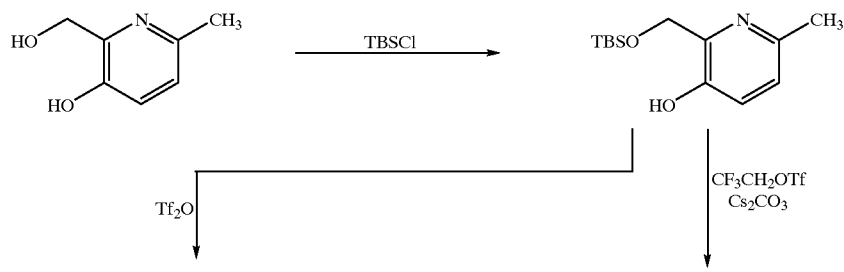

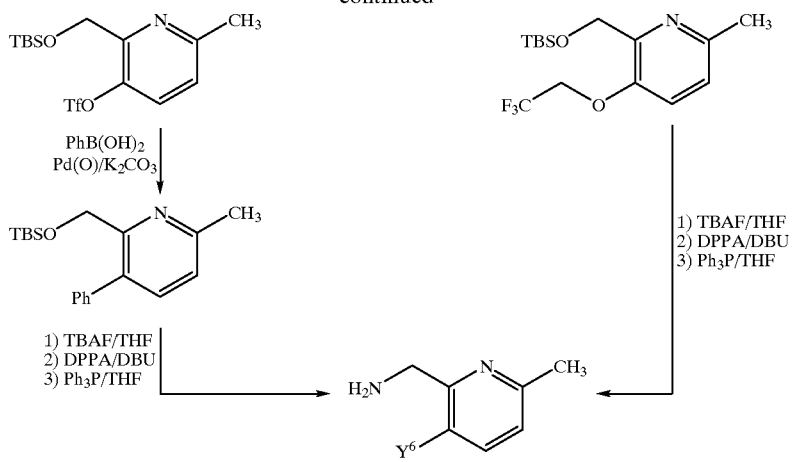

Modifications of the method will allow different $R^1$, $R^2$, and A groups contemplated by the scope of the broad claim below to be present by the use of an appropriate reagent or appropriately substituted starting material in the indicated synthetic step. Amino alcohols having different $R^1$ and $R^2$ groups can be prepared, for example, by a procedure such as the one below:

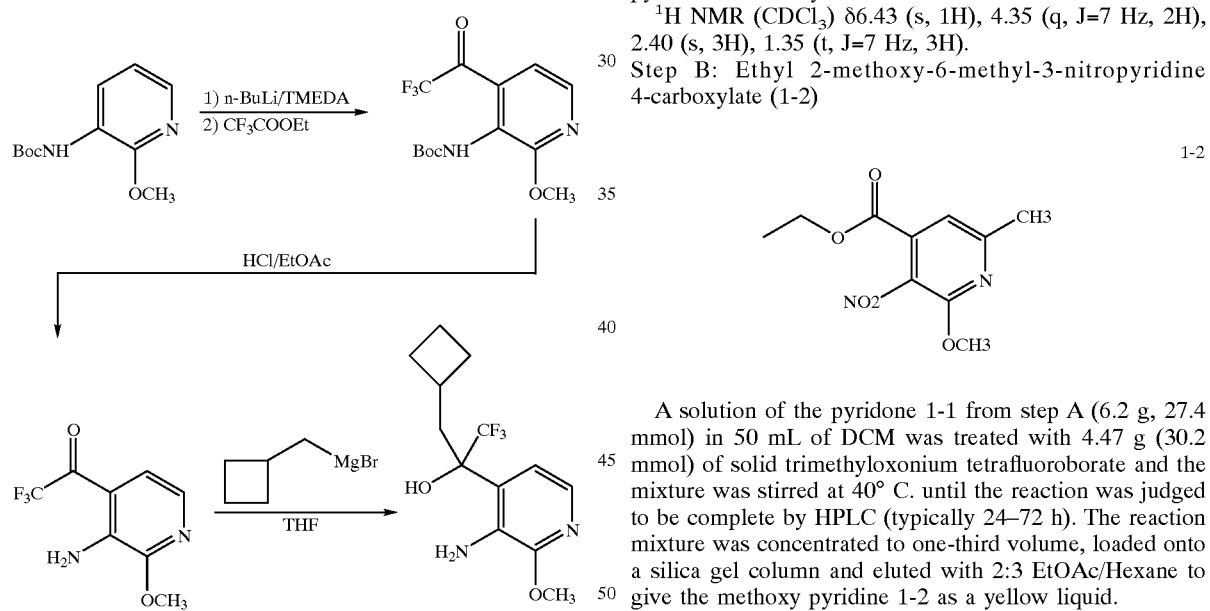

EXAMPLE 1

Step A: Ethyl 6-methyl-3-nitropyridone 4-carboxylate (1-1)

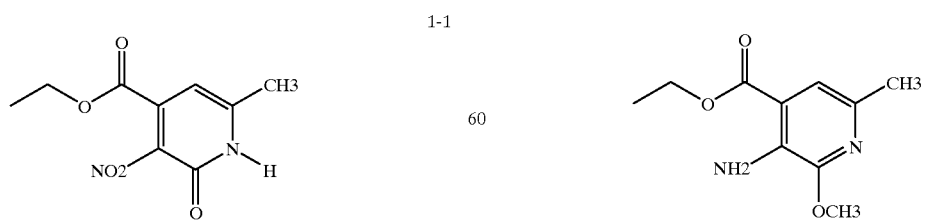

To a slurry nitroacetamide ammonia salt (70.3 g, 581 mmol) in 400 mL of deionized water was added 100 g (633 mmol, 1.09 equiv.) of ethyl 2,4-dioxovalerate followed by a solution of piperdinium acetate (prepared by adding 36 mL of piperdine to 21 mL of acetic acid in 100 mL of water). The resulting solution was stirred at 40° C. for 16 h then cooled in an ice bath. The precipitated product was filtered and washed with 50 mL, of cold waler to give the above pyridone 1-1 as a yellow solid.

$^1$H NMR (CDCl$_3$) δ6.43 (s, 1H), 4.35 (q, J=7 Hz, 2H), 2.40 (s, 3H), 1.35 (t, J=7 Hz, 3H).

Step B: Ethyl 2-methoxy-6-methyl-3-nitropyridine 4-carboxylate (1-2)

1-2

A solution of the pyridone 1-1 from step A (6.2 g, 27.4 mmol) in 50 mL of DCM was treated with 4.47 g (30.2 mmol) of solid trimethyloxonium tetrafluoroborate and the mixture was stirred at 40° C. until the reaction was judged to be complete by HPLC (typically 24–72 h). The reaction mixture was concentrated to one-third volume, loaded onto a silica gel column and eluted with 2:3 EtOAc/Hexane to give the methoxy pyridine 1-2 as a yellow liquid.

$^1$H NMR (CDCl$_3$) δ7.2 (s, 1H), 4.35 (q, J=7 Hz, 2H), 4.05 (s, 3H), 2.55 (s, 3H), 1.35 (t, J=7 Hz, 3H).

Step C: Ethyl 3-amino-2-methoxy-6-methylpyridine 4-carboxylate (1-3)

1-3

To an oxygen free solution of the nitro ester 1-2 from step B (2.5 g, 10.4 mmol) in 50 mL of EtOAc was added 520 mg of 10% Pd on charcoal. Hydrogen gas was added and the reaction mixture was stirred for 17 h. The solution was filtered through a pad of Celite, concentrated and chromatographed (2:3 EtOAc/Hexane) to give the desired amine 1-3 as a white solid.

$^1$H NMR (CDCl$_3$) δ7.05 (s, 1H), 5.70 (bs, 2H), 4.35 (q, J=7 Hz, 2H), 3.95 (s, 3H), 2.37 (s, 3H), 1.39 (t, J=7 Hz, 3H).

Step D: Amino alcohol 1-4

1-4

To a −70° C. solution of 260 mg (1.0 mmol) of the ester 1-3 from step C in 5 mL of THF was added 1.2 mL (3.5 mmol) of 3 M MeMgBr. The resulting solution was allowed to warm to ambient temperature over 16 h. The reaction mixture was quenched with 5 mL of saturated NH$_4$Cl solution and the two phases were separated. The aqueous phase was extracted with 10 mL of EtOAc and the combined organic extracts were washed with 5 mL of brine and dried over MgSO$_4$. The yellow solution was concentrated and chromatographed (1:1 EtOAc/Hexane) give alcohol 1-4.

$^1$H NMR (CDCl$_3$) δ6.45 (s, 1H), 4.60 (bs, 1H), 3.95 (s, 3H), 2.55 (s, 3H), 1.60 (s, 6H).

Step E: Oxazinone 1-5

1-5

To a solution of 386 mg (2.0 mmol) of the amino alcohol 1-4 from step D in 10 mL of THF was added 1.62 g (10.0 mmol) of 1,1'-carbonyl diimidazole. The resulting solution was heated at 55° C. over 16 h. The reaction mixture was cooled and the solvent was removed by rotory evaporation. The mixture was redissolved in 50 mL of EtOAc and washed sequentially with 10 mL each of saturated NH$_4$Cl solution, water, then brine. The solution was concentrated and chromatographed (1:1 EtOAc/Hexane) to give oxazinone 1-5.

$^1$H NMR (CDCl$_3$) δ7.17 (bs, 1H), 6.49 (s, 1H), 3.95 (s, 3H), 2.40 (s, 3H), 1.66 (s, 6H).

Step F: Pyridone 1-6

1-6

To 333 mg (1.5 mmol) of the oxazinone from step E was added 1.72 g (15.0 mmol) of solid pyridine hydrochloride. The solid mixture was heated at 155° C. for 5 min to effect a melt. The reaction mixture was cooled to rt, quenched with 10 mL of water and stirred for 20 min. The resulting precipitate was filtered and air dried to give pyridone 1-6.

$^1$H NMR (DMSO d$_6$) δ11.85 (bs, 1H), 9.30 (bs, 1H), 6.03 (s, 1H), 2.10 (s, 3H), 1.45 (s, 6H).

Step G: Benzyl Ester 1-7

1-7

To 186 mg (0.89 mmol) of the pyridone 1-6 from step F in 5 mL of DMF was added 325 mg (1.0 mmol) of Cs$_2$CO$_3$ and 0.158 mL (1.0 mmol) of benzyl 2-bromoacetate. The resulting mixture was stirred at rt for 15 h. The reaction mixture was then evaporated to dryness, redissolved in 20 mL of EtOAc and washed with 3×5 mL of brine. The organic solution was dried over MgSO$_4$ concentrated and chromatographed (EtOAc) to give benzyl ester 1-7.

$^1$H NMR (CDCl$_3$) δ7.45 (bs, 1H), 7.40–7.20 (m, 5H), 5.90 (s, 1H), 5.25 (s, 2H), 4.82 (s, 2H), 2.30 (s, 3H), 1.65 (s, 6H).

Step H: Carboxylic Acid 1-8

1-8

A solution containing 176 mg (0.492 mmol) of the ester 1-7 from step G and 50 mg of 10% Pd on carbon in 12 mL of THF and 6 mL of MeOH was hydrogenated at room temperature under a baloon of H$_2$. After stirring for 20 min, the reaction mixture was filtered through Celite and evaporated to dryness to give acid 1-8.

$^1$H NMR (DMSO d$_6$) δ13.2 (bs, 1H), 9.45 (s, 1H), 6.20 (s, 1H), 4.70 (s, 2H), 2.50 (s, 3H), 1.60 (s, 6H).

EXAMPLE 2

The following example shows a detailed procedure for obtaining an amino alcohol corresponding to compound 1-4 which has different substituents for $R^1$ and $R^2$.

Ketone 2-1

2-1

To a −70° C. solution of 1.12 g (5.0 mmol) of 3-(N-tertbutoxycarbonylamino)-2-methoxypyridine (Kelly, *Tetrahedron Lett.* 35 (48), 1994, 9003–9006) in 25 mL of dry ether was added 1.8 mL (12.0 mmol) TMEDA followed by 4.8 mL (12.0 mmol) of n-BuLi. The resulting solution was warmed to −15° C. where it was aged for 2 h. The reaction mixture was recooled to −70° C. and treated with 0.83 mL (7.0 mmol) of ethyl trifluoroacetate. After stirring an additional 3 h, the reaction was quenched with 25 mL of saturated NH₄Cl solution and the two phases were separated. The aqueous phase was extracted with 100 mL of EtOAc and the combined organic extracts were washed with 25 mL of brine and dried over MgSO₄. The yellow solution was concentrated and chromatographed (CH₂Cl₂) to afford trifluoromethyl ketone 2-1.

¹H NMR (CDCl₃) δ7.95 (d, J=8 Hz, 1H), 7.10 (bs, 1H), 6.95 (d, J=8Hz, 1H), 4.05 (s, 3H), 1.50 (s, 9H).

Amino ketone 2-2

2-2

A solution of 320 mg (1.0 mmol) of ketone 2-1 in 30 mL of EtOAc was saturated with gaseous HCl over 5 minutes at 0° C. The reaction mixture was stirred for 1 h then evaporated to dryness. The mixture was redissolved in 50 mL of saturated NaHCO₃ and wished with 3×50 gml, of EtOAc. The yellow solution was concentrated to afford amino ketone 2-2 as a yellow solid.

¹H NMR (CDCl₃) δ7.90 (d, J=8 Hz, 1H), 6.97 (d,J=8 Hz, 1H), 6.65 (bs, 2H), 3.95 (s, 3H).

Amino alcohol 2-3

2-3

To a −70° C. solution of 220 mg (1.0 mmol) of ketone 2-2 in 10 mL of THF was added 8 mL (4.0 mmol) of a 0.5 M ethereal solution of freshly prepared cyclobutylmethylmagnesium bromide. The reaction mixture was stirred to room temperature over 5 h and quenched with 10 mL of saturated NH₄Cl solution. The mixture was extracted with 3×50 gmL of EtOAc and dried over MgSO₄. Column chromatography (3:2 Hexane/EtOAc) afforded amino alcohol 2-3.

¹H NMR (CDCl3) δ7.60 (d, J=8 Hz, 1H), 6.60 (d, J=8 Hz, 1H), 4.60 (bs, 1H), 3.95 (s, 3H), 2.2–1.6 (m, 10 H).

EXAMPLE 3

Following the procedure of Example 1, but using cyclopropyl methylene magnesium bromide instead of methyl magnesium bromide used in Step D to make 1-4, the following compound was prepared 3-1

To a solution of carboxylic acid 1-8 (60 mg, 0.173 mmol) and 34.0 mg (0.173 mmol) of 3-fluoro-2-aminomethylpyridine in 1 mL of DMF was added 33.0 mg (0.173 mmol) of EDC, 23.0 mg (0.173 mmol) of HOBT and 0.076 mL of N-methylmorpholine. The reaction mixture was allowed to stir for 16 h before removal of the solvent in vacuo. The mixture was diluted with 10 mL of EtOAc and 2 mL water. The aqueous phase was discarded and the organic solution was washed with 3×1 mL of water then 1 mL of brine. Evaporation of the solvent and addition of methanolic HCl gas provided compound 3-1 as a white solid.

¹H NMR (CD3OD) δ8.50 (bs, 1H), 9.45 (bs, 1H), 7.85 (m, 1H), 7.62 (m, 1H), 6.21 (s, 1H), 4.95 (s, 2H), 4.65 (s, 2H), 2.38 (s, 3H), 2.10 (dd, J=5.5 Hz, 14.8 Hz, 2H), 1.60 (m, 2H), 0.65 (m, 2H), 0.44 (m, 4H), 0.33 (m, 2H), 0.05 (m, 2H).

Anal. Calc'd for C,H,N: C, 58.71; H, 5.75; N, 11.41. Found: C, 58.92; H, 6.04; N, 11.24.

LRMS (M+1): 455.2.

EXAMPLE 4

Tablet Preparation

Tablets containing 25.0, 50.0, and 100.0 mg., respectively, of the following active compounds are prepared as illustrated below (compositions A–C). Active I is compound 3-1.

|  | Amount-mg | | |
| --- | --- | --- | --- |
| Component | A | B | C |
| Active I | 25 | 50 | 100 |
| Micro-crystalline cellulose | 37.25 | 100 | 200 |
| Modified food corn starch | 37.25 | 4.25 | 8.5 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 5

Tablet Preparation

Exemplary compositions of compound 3-1 tablets are shown below:

| Component | 0.25 mg | 2 mg | 10 mg | 50 mg |
|---|---|---|---|---|
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

Active I is compound 3-1. 2, 10 and 50 mg tablets are film-coated with an aqueous dispersion of hydroxypropyl cellulose, hydroxypropyl methylcellulose and titanium dioxide, providing a nominal weight gain of 2.4%.

Tablet Preparation Via Direct Compression

Active I, mannitol and microcrystalline cellulose are sieved through mesh screens of specified size (generally 250 to 750 μm) and combined in a suitable blender. The mixture is subsequently blended (typically 15 to 30 min) until the drug was uniformly distributed in the resulting dry powder blend. Magnesium stearate is screened and added to the blender, after which a precompression tablet blend is achieved upon additional mixing (typically 2 to 10 min). The precompression tablet blend is then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets are dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 6

Intravenous Formulations

Intravenous formulations of compound 3-1 are prepared according to general intravenous formulation procedures. Active I is compound 3-1.

| Component | Estimated range |
|---|---|
| Active I | 0.12–0.61 mg |
| D-glucuronic acid* | 0.5–5 mg |
| Mannitol NF | 50–53 mg |
| Water for injection | q.s. 1.0 mL |

1N sodium hydroxide is used to achieve a solution pH in the range of between 3.9–4.1.

Exemplary compositions A–C are as follows:

| Component | A | B | C |
|---|---|---|---|
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base;
**0.25 mg free base;
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the formula:

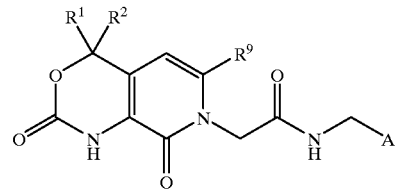

or a pharmaceutically acceptable salt thereof, wherein
A is

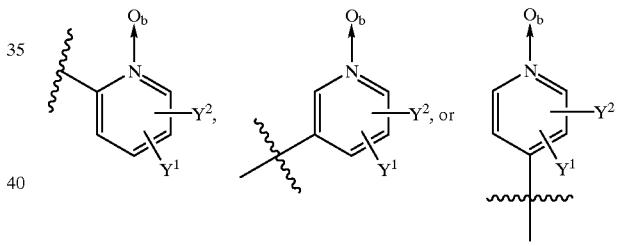

wherein
$Y^1$ and $Y^2$ are independently
  hydrogen,
  $C_{1-4}$ alkyl,
  $C_{1-4}$ alkoxy,
  $F_u H_v C(CH_2)_{0-1} O—$, wherein u and v are either 1 or 2, provided that when u is 1, v is 2, and when u is 2, v is 1,
  $C_{3-7}$ cycloalkyl,
  halogen,
  cyano, or
  trifluoromethyl, and
  wherein b is 0 or 1; and
$R^1$ and $R^2$ are independently
  hydrogen,
  phenyl, unsubstituted or substituted with one or more of $C_{1-4}$ alkyl, $C_{1-4}$ alkoxy, halogen, hydroxy, COOH, $CONH_2$, $CH_2OH$, $CO_2R^8$, where $R^8$ is $C_{1-4}$ alkyl, or $SO_2NH_2$,
  $CHR^6R^7$
    wherein $R^6$ and $R^7$ are independently
      hydrogen,
      unsubstituted $C_{1-4}$ alkyl, C$_{1-4}$ alkyl substituted with OH, COOH, NH$_2$, aryl, CF$_3$,
C$_{3-7}$ cycloalkyl,
CF$_3$
CH$_2$C$_{3-7}$ cycloalkyl, unsubstituted or substituted with aryl,
C$_{7-12}$ bicyclic alkyl, or
C$_{10-16}$ tricyclic alkyl; and
R$^9$ is C$_{1-4}$ alkyl.

2. A compound of claim 1, or a pharmaceutically acceptable salt thereof, includes those wherein A is

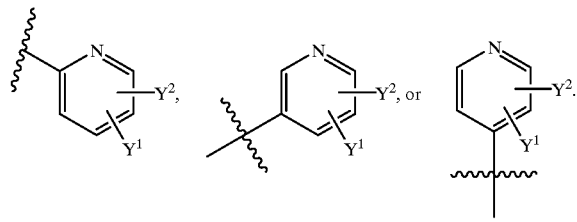

3. A compound of claim 2, or a pharmaceutically acceptable salt thereof, includes those wherein A is

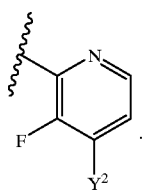

4. A compound of claim 3, or a pharmaceutically acceptable salt thereof, wherein R$^1$ and R$^2$ are independently
—CH$_3$,
—CH$_2$CH(CH$_3$)$_2$,
—CH$_2$CH$_3$,
—CH(CH$_3$)$_2$, or

R$^9$ is CH$_3$.

5. A compound of claim 4, or a pharmaceutically acceptable salt thereof, which is

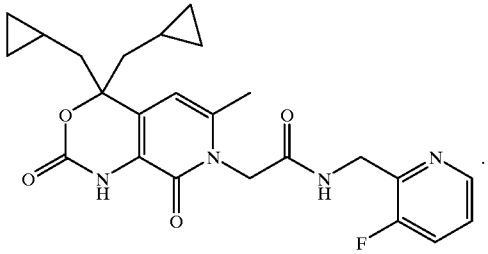

6. A compound of claim 5 which is

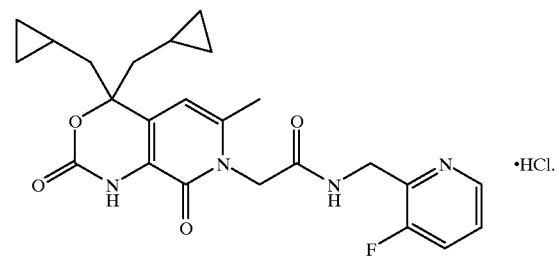

7. A pharmaceutical composition comprising a therapeutically effective amount of a compound of claim 1.

8. A method for inhibiting thrombus formation in blood in a patient comprising administering to the patient in need thereof a thrombin formation inhibiting amount of a composition of claim 7.

* * * * *